(12) United States Patent
Lee et al.

(10) Patent No.: US 11,432,765 B2
(45) Date of Patent: Sep. 6, 2022

(54) EXCREMENT CARE ROBOT WITH INTEGRATED ANALYSIS FUNCTION FOR MOTION AND CONDITION OF BEDRIDDEN PATIENT

(71) Applicant: CURACO, Inc., Seongnam-si (KR)

(72) Inventors: Hoonsang Lee, Gwangju-si (KR); Hosang Lee, Seoul (KR); Sungpil Choi, Seoul (KR); Dounghoon Lee, Gwangju-si (KR)

(73) Assignee: CURACO, Inc., Seongnam-si (KR)

( * ) Notice: Subject to any disclaimer, the term of this patent is extended or adjusted under 35 U.S.C. 154(b) by 181 days.

(21) Appl. No.: 16/953,374

(22) Filed: Nov. 20, 2020

(65) Prior Publication Data

US 2021/0187753 A1 Jun. 24, 2021

(30) Foreign Application Priority Data

Dec. 18, 2019 (KR) .......................... 10-2019-0169829

(51) Int. Cl.
*A61F 5/44* (2006.01)
*A61B 5/00* (2006.01)
(Continued)

(52) U.S. Cl.
CPC ............ *A61B 5/6802* (2013.01); *A61B 5/1117* (2013.01); *A61G 9/02* (2013.01); *B25J 11/009* (2013.01)

(58) Field of Classification Search
CPC ........... A61B 5/00; A61B 5/11; A61B 5/1117; A61B 5/6802; A61F 5/44; A61F 1/4405; A61F 5/442; A61F 5/443; A61F 13/15; A61F 13/20; A61F 13/42; A61F 13/44; A61F 13/82; A61G 9/00; A61G 9/02;
(Continued)

(56) References Cited

U.S. PATENT DOCUMENTS

| 4,723,952 A * | 2/1988 | Esposito ................. A61F 5/449 604/338 |
| 6,407,308 B1 * | 6/2002 | Roe .......................... A61L 15/18 604/362 |

(Continued)

FOREIGN PATENT DOCUMENTS

KR 10-0893733 B1 4/2009

OTHER PUBLICATIONS

NPL Search {Jul. 8, 2022).*

*Primary Examiner* — Van T Trieu
(74) *Attorney, Agent, or Firm* — Revolution IP, PLLC

(57) ABSTRACT

Disclosed is an excrement care robot with an integrated analysis function on the motion and condition of a bedridden patient including: a body-fitted type treating apparatus including a body which has a shape corresponding to bends of the genitals and buttocks of a human body and is formed with a treatment space that is opened in a direction of the genitals and buttocks of the human body to receive excrement discharged from the human body, a discharge unit which is provided in the body and communicates with the treatment space to discharge the excrement of the treatment space to the outside, and a sensor unit that is provided in the body to measure a direction of movement of the body; and a motion analysis unit that receives sensor data of the sensor unit to analyze the motion of the human body through the movement of the body.

10 Claims, 5 Drawing Sheets

(51) Int. Cl.
*A61B 5/11* (2006.01)
*A61G 9/02* (2006.01)
*B25J 11/00* (2006.01)

(58) Field of Classification Search
CPC ........ H01M 1/00; H01M 10/04; H01M 10/54; B25J 11/00
See application file for complete search history.

(56) References Cited

U.S. PATENT DOCUMENTS

2011/0308017 A1* 12/2011 Nakamura ............... A61G 9/00
5/605
2022/0133522 A1* 5/2022 Chopra ................. A61F 5/4407
604/335

* cited by examiner

EXCREMENT CARE ROBOT WITH INTEGRATED ANALYSIS FUNCTION FOR MOTION AND CONDITION OF BEDRIDDEN PATIENT

CROSS-REFERENCE TO RELATED APPLICATION

This application claims under 35 U.S.C. § 119(a) the benefit of Korean Patent Application No. 10-2019-0169829 filed on Dec. 18, 2019, the entire contents of which are incorporated herein by reference.

BACKGROUND

(a) Technical Field

The present invention relates to an excrement care robot which is formed to be wearable on a human body to treat excrement, and more particularly, to an excrement care robot which is formed to perform an integrated analysis of the motion and condition of a bedridden patient to quantify a position change of the bedridden patient and induce an appropriate pressure distribution based on a position change history.

(b) Background Art

In general, people such as patients, the elderly, etc., who have difficulty in moving or who have difficulty moving their lower bodies at will, have no ability capable of treating excrement on their own, so that there is a discomfort that a guardian or caregiver must always reside around the people.

Therefore, in order to solve such discomfort, the research and development of an excrement treating apparatus that comes into direct contact with a human body to collect the excrement have been conducted. Such an excrement treating apparatus is designed to receive the user's excrement, suck the received excrement, and then discharge the sucked excrement to the outside, so that the excrement can be automatically treated even if a guardian or caregiver does not reside around the user.

However, conventional excrement treating apparatuses which have been developed up to date often focus on only an excrement treatment function, and are designed without considering the user's body, and thus, there is a problem that the usability is very poor. In general, the periphery of the buttocks or genitals from which the excrement is excreted has a structure that is difficult to be in close contact with the excrement treating apparatus due to severe bends, and accordingly, there are many cases where the excrement leaks between the human body and the excrement treating apparatus.

In addition, users who use an excrement treating apparatus, such as patients or the elderly, often live while lying on a bed, and cannot change their positions by themselves in many cases. When such a condition persists for a long time, bedsores and the like occur, and thus, it is necessary to change a position periodically. However, since the users could not change the positions while wearing the excrement treating apparatus, there was an inconvenience to remove the excrement treating apparatus.

Therefore, there is a need for a method for solving these problems.

PRIOR ART DOCUMENT

Patent Document (Patent Document 0001) Korean Patent No. 10-0893733

The above information disclosed in this Background section is only for enhancement of understanding of the background of the invention and therefore it may contain information that does not form the prior art that is already known in this country to a person of ordinary skill in the art.

SUMMARY OF THE DISCLOSURE

The present invention has been made in an effort to solve the above-described problems associated with prior art. An object of the present invention is to induce an appropriate pressure distribution in a body of a bedridden patient by performing an integrated analysis on the motion and condition of the bedridden patient.

The objects of the present invention are not limited to the aforementioned objects, and other objects, which are not mentioned above, will be apparent to those skilled I in the art from the following description.

In order to achieve the objects described above, according to an embodiment of the present invention, there is provided an excrement care robot with an integrated analysis function on the motion and condition of a bedridden patient including: a body-fitted type treating apparatus including a body which has a shape corresponding to bends of the genitals and buttocks of a human body and is formed with a treatment space that is opened in a direction of the genitals and buttocks of the human body to receive excrement discharged from the human body, a discharge unit which is provided in the body and communicates with the treatment space to discharge the excrement of the treatment space to the outside, and a sensor unit that is provided in the body to measure a direction of movement of the body; and a motion analysis unit that receives sensor data of the sensor unit to analyze the motion of the human body through the movement of the body.

The sensor unit may include an inertial sensor that measures rotation angles with respect to a X (pitch) axis, a Y (roll) axis, and a Z (yaw) axis of the body.

In addition, the motion analysis unit may determine that a user takes a position of lying on his/her side when an amount of change in rotation angle of the X-axis is less than a first angle range in a + direction or − direction within a predetermined first time range.

Further, the motion analysis unit may determine that the user is in a poor wearing condition when the amount of change in rotation angle of the X-axis is equal to or greater than the first angle range in the + direction or − direction within the predetermined first time range.

Furthermore, the motion analysis unit determines that the user takes a sitting position or is in a poor wearing condition when the amount of change in rotation angle of the Y-axis is equal to or greater than a second angle range in the— direction within a predetermined second time range.

In addition, the motion analysis unit determines that the user is in a removal condition or is in a poor wearing condition when the amount of change in rotation angle of the Y-axis is equal to or greater than the second angle range in the + direction within the predetermined second time range.

Further, the motion analysis unit may determine that the user is in a removal condition or in a poor wearing condition when the amount of change in rotation angle of the Z-axis is equal to or greater than a third angle range in a + direction or − direction within a predetermined third time range.

In addition, the motion analysis unit may determine that the user is in any one of a fall condition, an emergency condition, or a removal condition when the amount of change in rotation angle of the X-axis is equal to or greater than the first angle range in the + direction or − direction, the amount of change in rotation angle of the Y-axis is equal to or greater than the second angle range in the + direction or − direction, and the amount of change in rotation angle of the Z-axis is equal to or greater than the third angle range in the + direction or − direction.

Meanwhile, the motion analysis unit may generate history information on position change of the user over time through the sensor data measured by the sensor unit.

The excrement care robot of the present invention may further include a communication unit that transmits the sensor data measured by the sensor unit to the motion analysis unit.

According to the present invention to solve the problems, in the excrement care robot with the integrated analysis function on the motion and condition of the bedridden patient, the sensor unit and the motion analysis unit are formed to perform an integrated analysis on the motion and condition of the bedridden patient to qualify a position change of the bedridden patient and induce an appropriate pressure distribution based on a position change history.

The effects of the present invention are not limited to the aforementioned effect, and other effects not mentioned above will be clearly understood to those skilled in the art from the description of the appended claims.

BRIEF DESCRIPTION OF THE DRAWINGS

The above and other features of the present invention will now be described in detail with reference to certain exemplary embodiments thereof illustrated the accompanying drawings which are given hereinbelow by way of illustration only, and thus are not limitative of the present invention, and wherein.

Figure 1:
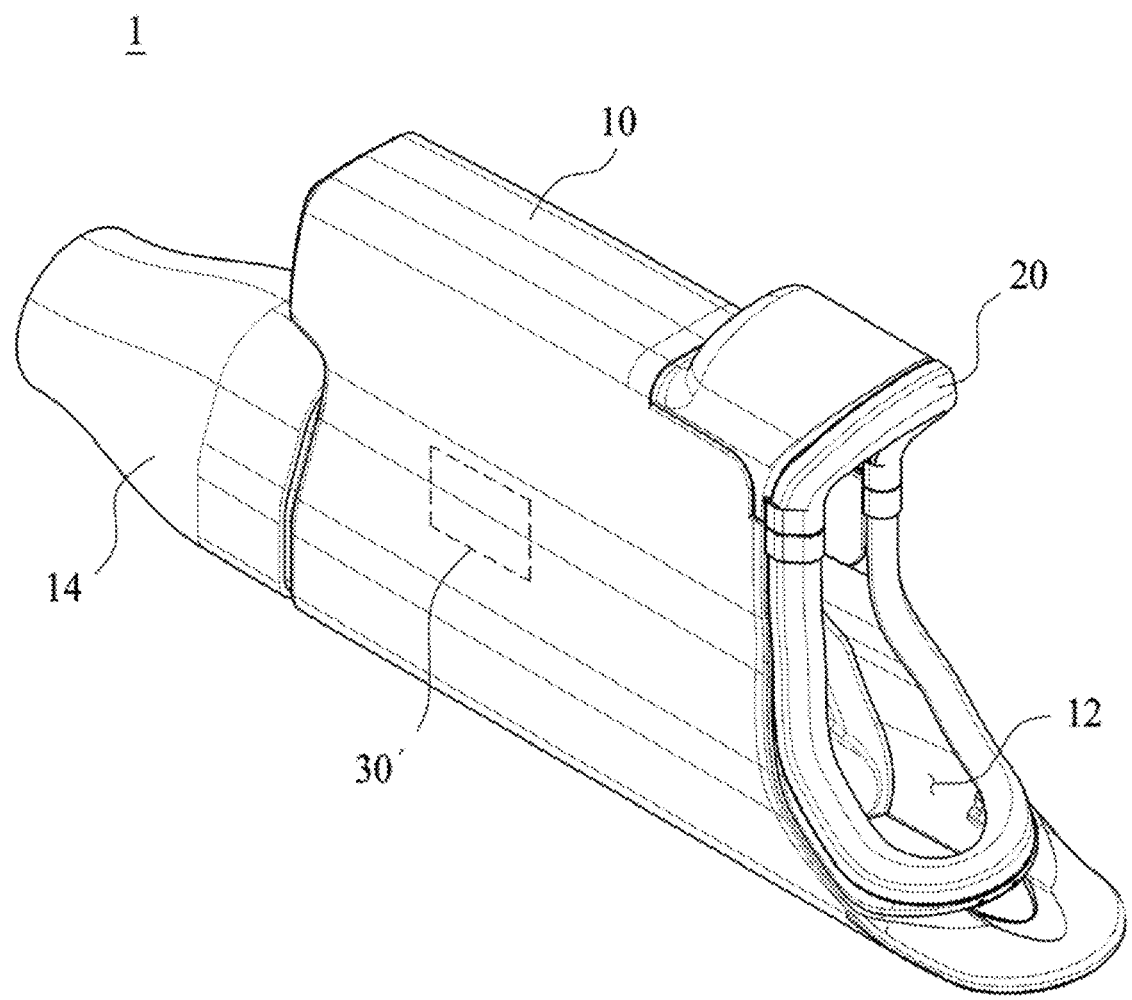
FIG. 1 is a view illustrating an appearance of a body-fitted type treating apparatus in an excrement care robot according to an embodiment of the present invention.

It should be understood that the appended drawings are not necessarily to scale, presenting a somewhat simplified representation of various preferred features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Hereinafter, a preferred embodiment of the present invention, of which an object of the present invention may be realized in detail, will be described with reference to the accompanying drawings. In describing the embodiment, like names and like reference numerals will be used with respect to like components and the resulting additional description will be omitted.

Figure 2:
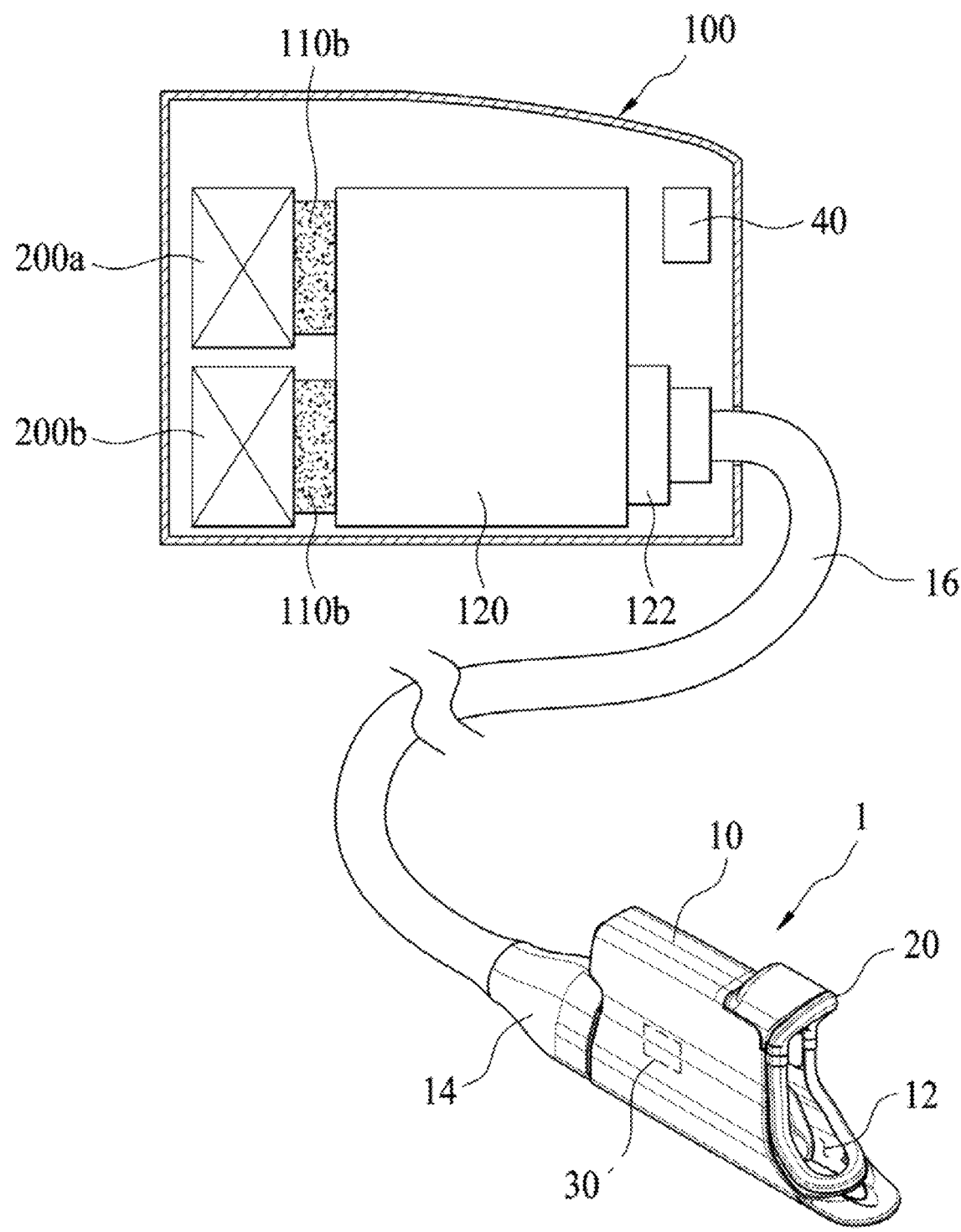
FIG. 2 is a view illustrating all components of the excrement care robot according to an embodiment of the present invention.

FIG. 1 is a view illustrating an appearance of a body-fitted type treating apparatus in an excrement care robot according to an embodiment of the present invention and FIG. 2 is a view illustrating all components of the excrement care robot according to an embodiment of the present invention.

As illustrated in FIGS. 1 to 2, an excrement care robot according to an embodiment of the present invention includes a body-fitted type treating apparatus 1 that is a component directly worn by a user, that is, a bedridden patient, and a main treating device 100 connected to the body-fitted type treating apparatus.

In addition, the body-fitted type treating apparatus 1 includes a body 10, a discharge unit 14, a contact member 20, and a sensor unit 30.

The body 10 has a shape corresponding to bends of the genitals and buttocks of a human body, and includes a fitting part formed with a treatment space 12 that is opened in a direction of the genitals and buttocks of the human body to receive excrement discharged from the human body, and a main body part which is connected to the fitting part so as to be fitted between the legs of the human body and has a receiving space formed therein.

Here, the genitals of the human body refer to an area around the genitals of men and women, and the buttocks refer to an area around the anus connected with the genitals. That is, the fitting part is formed to be fitted on the groin of the human body, and has a curved shape to correspond to the bends thereof.

In addition, in order to maximize the wearing feeling when the fitting part is fitted on the human body, the fitting part may include the contact member 20 having elasticity.

In addition, although not illustrated in the drawing, a receiving space is provided inside the main body part, and various components required for the excrement treating apparatus may be provided in the receiving space. As such, the components provided in the receiving space are obvious to those skilled in the art, and since the structure thereof may be variously formed without limitation, a detailed description thereof will be omitted.

The discharge unit 14 is provided at the rear of the body 10 and communicates with the treatment space 12 through a discharge passage to discharge the excrement of the treatment space 12 to the outside.

In particular, in the embodiment, the discharge unit 14 protrudes to the rear side of the body 10 to be provided on the main treating device 100 side, and may be connected with a waste tank 120 having a collection space formed therein so that the excrement discharged by the discharge unit 14 is collected through an excrement flow hose 16.

In addition, the excrement is sucked into the waste tank 120 side by a suck force generated from blow motors 200a and 200b which are provided in the main treating device 100 to provide a vacuum suck force on the flow passage of the excrement.

Figure 3:
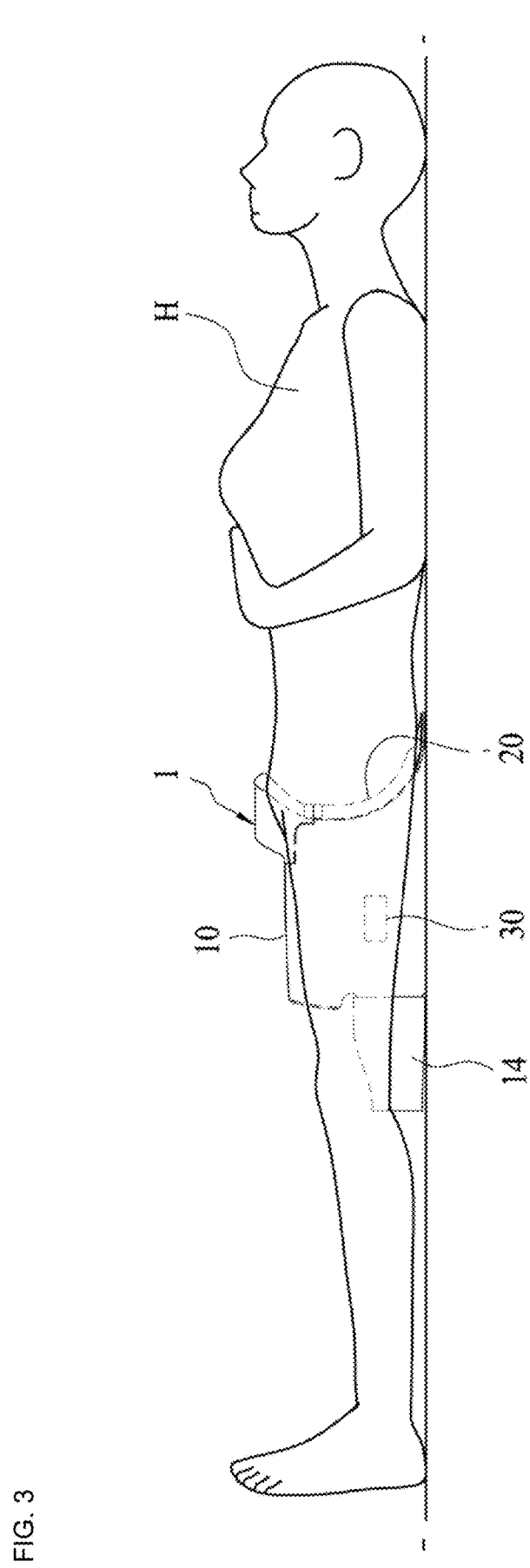
FIG. 3 is a view illustrating an appearance of wearing the body-fitted type treating apparatus on a human body in the excrement care robot according to an embodiment of the present invention.

Meanwhile, as illustrated in FIG. 3, a user H may stably wear the body-fitted type treating apparatus 1 of the excrement care robot by contacting a fitting part of the body 10 of the body-fitted type treating apparatus 1 with the genitals and buttocks in a state lying on a bed and extending user's legs to both sides of the main body part.

As such, since the body-fitted type treating apparatus 1 of the excrement care robot according to the embodiment is formed to correspond to the shape of the human body, the user H does not need to forcefully change a position in accordance with the body-fitted type treating apparatus 1, but may maintain a natural position.

Referring to FIGS. 1 to 3, the excretion care robot according to an embodiment of the present invention further includes a sensor unit 30, a motion analysis unit (not illustrated), and a communication unit 40

The sensor unit 30 is provided on the body 10 of the body-fitted type treating apparatus 1 and serves to measure a direction of movement of the body 10.

At this time, in the embodiment, the sensor unit 30 may include an inertial sensor that measures rotation angles with respect to a pitch axis, a roll axis, and a yaw axis of the body 10. In other words, the sensor unit 30 may derive a position change of the bedridden patient based on the three-axis movement angles.

The motion analysis unit is a component that receives sensor data of the sensor unit 30 and analyzes the motion of the human body through the movement of the body 10, and may be provided in various positions.

For example, the motion analysis unit may be directly embedded in the body 10 of the body-fitted type treating apparatus 1, or also provided on the main treating device 100 side. Alternatively, the motion analysis unit may also be provided in an external terminal or the like separately from the body-fitted type treating apparatus 1 and the main treating device 100.

In the embodiment, the motion analysis unit is illustrated as being provided in the external terminal. Accordingly, in the embodiment, the communication unit 40 transmits the sensor data measured by the sensor unit 30 to the motion analysis unit.

Here, the communication unit 40 may also be directly embedded in the body 10 of the body-fitted type treating apparatus 1, or also provided on the main treating device 100 side. Alternatively, the communication unit 40 may also be provided in an external terminal or the like separately from the body-fitted type treating apparatus 1 and the main treating device 100.

In the case of the embodiment, the communication unit 40 is illustrated as being provided on the main treating device 100.

Figure 4:
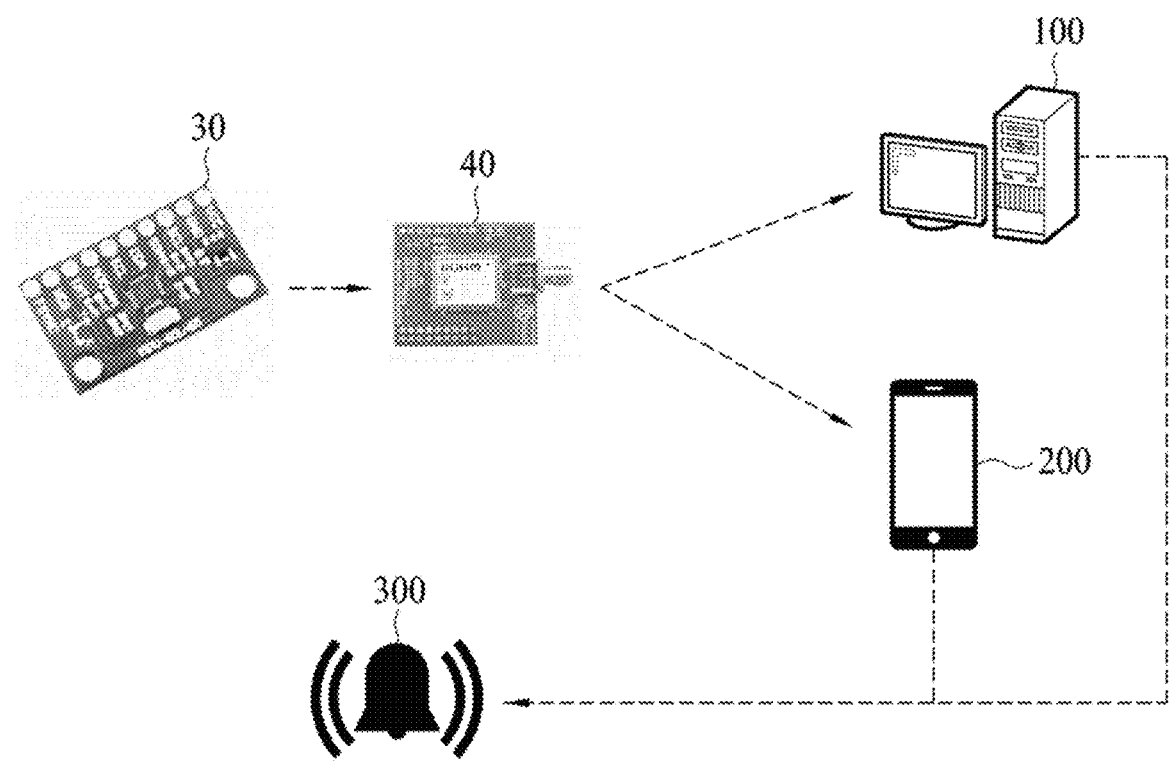
FIG. 4 is a view schematically illustrating a data flow through the excrement care robot according to an embodiment of the present invention.

FIG. 4 is a view schematically illustrating a data flow through the excrement care robot according to an embodiment of the present invention.

As illustrated in FIG. 3, in the embodiment, the sensor data generated by the sensor unit 30 may be transmitted to at least one of a management server 310 and a user terminal 320 in the form of a smartphone through the communication unit 40 in a wired or wireless communication manner.

As described above, the motion analysis unit may be directly embedded in the excrement care robot, but may be separately provided in an external terminal or the like.

In the embodiment, the motion analysis unit is provided in the management server 310 and the user terminal 320, and the sensor data transmitted through the communication unit 40 may be analyzed by the motion analysis unit. In addition, the motion analysis unit may generate history information on position change of the user over time while monitoring a patient's condition in real time through the sensor data measured by the sensor unit.

In particular, when it is determined that an emergency situation or the like has occurred during the monitoring process for the patient, the motion analysis unit may perform an alarm through an alarm unit 300 provided at various locations.

Hereinafter, a method capable of accurately analyzing the condition of a user, that is, a bedridden patient by the motion analysis unit will be described.

Figure 5:
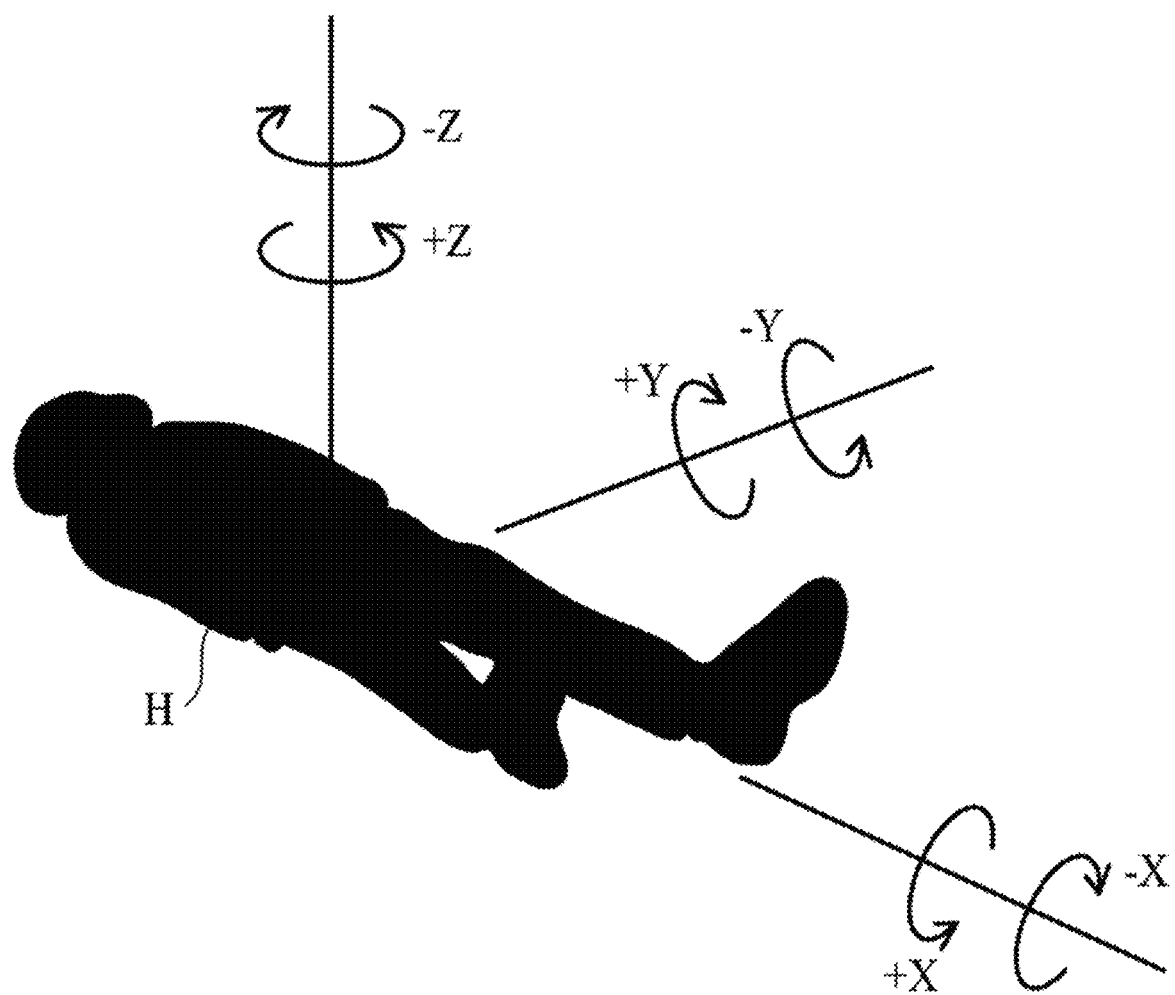
FIG. 5 is a view illustrating a 3-axis based body rotation concept of a user wearing the body-fitted type treating apparatus of the excrement care robot according to an embodiment of the present invention.

FIG. 5 is a view illustrating a 3-axis based body rotation concept of a user wearing the body-fitted type treating apparatus 1 of the excrement care robot according to an embodiment of the present invention.

As described above, the sensor unit 30 may include an inertial sensor, and the inertial sensor may measure rotation angles with respect to an X (pitch) axis, a Y (roll) axis, and a Z (yaw) axis of the body 10.

Accordingly, according to the present invention, it is possible to determine the left and right movement and the front and rear movement of the bedridden patient while lying down on a bed, etc., and to determine a risk of falling and a form of position change.

In addition, according to the present invention, it is possible to determine the patient's motion in detail even when the bedridden patient performs external activities or care activities while leaving the bed.

First, the motion analysis unit may determine that a user H takes a position of lying on his/her side when an amount of change in rotation angle of the X-axis is less than a first angle range in a + direction or − direction within a predetermined first time range.

This is because the X-axis corresponds to the left and right motion of the human body, and when the angle change in the X-axis is made within the predetermined range, the user H is considered in a normal condition.

However, when the amount of change in rotation angle of the X-axis is equal to or greater than the first angle range in the + direction or − direction within the predetermined first time range, the motion analysis unit may determined that the user H is in a poor wearing condition in which the user H does not normally wear the body-fitted type treating apparatus 1 of the excrement care robot.

This is a case in which the angle change in the X-axis of the user is greater than the angle change that may be made during a general position change, and it is determined that the user H is a poor wearing condition and thus, following measures may be performed.

Next, the motion analysis unit determines that the user H takes a sitting position or is in a poor wearing condition when the amount of change in rotation angle of the Y-axis is equal to or greater than a second angle range in the − direction within a predetermined second time range.

This is because the Y-axis may be determined to correspond to the movement of the head or legs of the human body.

Further, the motion analysis unit determines that the user H is in a removal condition or in a poor wearing condition when the amount of change in rotation angle of the Y-axis is equal to or greater than the second angle range in the + direction within the predetermined second time range.

In other words, when the amount of change in rotation angle of the Y-axis is in the + direction, it is difficult to come out in a normal position. Accordingly, this situation is because it is considered that the user H does not properly wear the body-fitted type treating apparatus 1 of the excrement care robot.

Further, the motion analysis unit may determine that the user H is in a removal condition or in a poor wearing condition when the amount of change in rotation angle of the Z-axis is equal to or greater than a third angle range in a + direction or − direction within a predetermined third time range. This is because, when the user H is lying on the bed normally, a change in rotation angle of the Z-axis hardly occurs.

Meanwhile, the motion analysis unit may determine that the user H is currently in any one of a fall condition, an emergency condition, or a removal condition when the amount of change in rotation angle of the X-axis is equal to or greater than the first angle range in the + direction or − direction, the amount of change in rotation angle of the Y-axis is equal to or greater than the second angle range in the + direction or − direction, and the amount of change in rotation angle of the Z-axis is equal to or greater than the third angle range in the + direction or − direction.

This is because a sudden change in rotation angle has occurred in all three axes, and it may be considered that a serious change has occurred in the body position of the user H.

As described above, in the present invention, the sensor unit and the control unit are formed to perform an integrated analysis on the motion and condition of the bed patient to qualify a position change of the bedridden patient.

Furthermore, the present invention has an advantage of inducing an appropriate pressure distribution based on the quantified position change history, and preventing bedsores and the like that may occur when the user H maintains the same position for a long time.

As described above, the prepared embodiment of the present invention has been as described, and in addition to the embodiments described above, a fact that the present invention can be materialized in other specific forms without departing from the gist or scope thereof will be apparent to those skilled in the art. Therefore, the aforementioned embodiments are not limited but should be considered to be illustrative, and accordingly, the present invention is not limited to the above description and may be modified within the scope of the appended claims and a range equivalent thereto.

What is claimed is:

1. An excrement care robot with an integrated analysis function on the motion and condition of a bedridden patient, the excrement care robot comprising:
  a body-fitted type treating apparatus including a body which has a shape corresponding to bends of the genitals and buttocks of a human body and is formed with a treatment space that is opened in a direction of the genitals and buttocks of the human body to receive excrement discharged from the human body, a discharge unit which is provided in the body and communicates with the treatment space to discharge the excrement of the treatment space to the outside, and a sensor unit that is provided in the body to measure a direction of movement of the body; and
  a motion analysis unit that receives sensor data of the sensor unit to analyze the motion of the human body through the movement of the body.

2. The excrement care robot of claim 1, wherein the sensor unit comprises an inertial sensor that measures rotation angles with respect to a X (pitch) axis, a Y (roll) axis, and a Z (yaw) axis of the body.

3. The excrement care robot of claim 2, wherein the motion analysis unit determines that a user takes a position of lying on his/her side when an amount of change in rotation angle of the X-axis is less than a first angle range in a + direction or − direction within a predetermined first time range.

4. The excrement care robot of claim 2, wherein the motion analysis unit determines that the user is in a poor wearing condition when the amount of change in rotation angle of the X-axis is equal to or greater than the first angle range in the + direction or − direction within the predetermined first time range.

5. The excrement care robot of claim 2, wherein the motion analysis unit determines that the user takes a sitting position or is in a poor wearing condition when the amount of change in rotation angle of the Y-axis is equal to or greater than a second angle range in the − direction within a predetermined second time range.

6. The excrement care robot of claim 2, wherein the motion analysis unit determines that the user is in a removal condition or in a poor wearing condition when the amount of change in rotation angle of the Y-axis is equal to or greater than the second angle range in the + direction within the predetermined second time range.

7. The excrement care robot of claim 2, wherein the motion analysis unit determines that the user is in a removal condition or in a poor wearing condition when the amount of change in rotation angle of the Z-axis is equal to or greater than a third angle range in a + direction or − direction within a predetermined third time range.

8. The excrement care robot of claim 2, wherein the motion analysis unit determines that the user is in any one of a fall condition, an emergency condition, or a removal condition when the amount of change in rotation angle of the X-axis is equal to or greater than the first angle range in the + direction or − direction, the amount of change in rotation angle of the Y-axis is equal to or greater than the second angle range in the + direction or − direction, and the amount of change in rotation angle of the Z-axis is equal to or greater than the third angle range in the + direction or − direction.

9. The excrement care robot of claim 1, wherein the motion analysis unit generates history information on position change of the user over time through the sensor data measured by the sensor unit.

10. The excrement care robot of claim 1, further comprising:
  a communication unit that transmits the sensor data measured by the sensor unit to the motion analysis unit.

* * * * *